(12) United States Patent
Yamamoto et al.

(10) Patent No.: US 7,067,476 B2
(45) Date of Patent: Jun. 27, 2006

(54) PEPTIDE DERIVATIVE, AND PHARMACEUTICALLY ACCEPTABLE SALT THEREOF, PROCESS FOR PRODUCING THE SAME, AND USE THEREOF

(75) Inventors: Kenji Yamamoto, Fukuoka (JP); Yoshimitsu Suda, Tokorozawa (JP); Tetsuji Asao, Kokubunji (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 10 days.

(21) Appl. No.: 10/493,060

(22) PCT Filed: Nov. 14, 2002

(86) PCT No.: PCT/JP02/11860

§ 371 (c)(1),
(2), (4) Date: Apr. 29, 2004

(87) PCT Pub. No.: WO03/042237

PCT Pub. Date: May 22, 2003

(65) Prior Publication Data

US 2004/0214780 A1    Oct. 28, 2004

(30) Foreign Application Priority Data

Nov. 16, 2001    (JP) .............................. 2001-352012

(51) Int. Cl.
*A01N 61/00* (2006.01)
*A61K 38/00* (2006.01)

(52) U.S. Cl. .......................................... 514/2; 530/300

(58) Field of Classification Search ..................... None
See application file for complete search history.

(56) References Cited

FOREIGN PATENT DOCUMENTS

| JP | 5-97708 | 4/1993 |
|----|---------|--------|
| JP | 11-139947 | 5/1999 |
| JP | 11-228526 | 8/1999 |
| JP | 11-335274 | 12/1999 |
| JP | 2000-191487 | 7/2000 |
| WO | WO 02/36551 A1 | 5/2002 |

OTHER PUBLICATIONS

Kadowaki, Tomoko et al; "Suppression of Virulence of *Porphyromonas gingivalis* by Potent Inhibitors Specific for Gingipains"; Current Protein and Peptide Science, vol. 4, No. 6 (2003) pp 451-458.
Gusman, Heloisa et al; "Salivary Histatin 5 Is Inhibitor of Both Host and Bacterial Enzymes Implicated in Periodontal Disease"; Infection and Immunity; Mar. 2001, pp 1402-1408.
European Search Report dated May 2, 2005.
Baba et al "New perspective of periodental disease research"; Tissue Culture Eng., 27 (9): pp343-347, 2001 (partial English Translation).
Pike et al "Lysine-and Arginine-specific Proteinases from *Porphyromonas gingivalis*"; J. of Biological Chem. vol. 269 No. 1 (Jan. 7, 1994) pp406-411.
Shah et al; Biology of the Species *Porphyromonas gingivalis*; CRC Press, Inc. 1993; pp227-243.
Dzink et al "The predominant cultivable microbiota of active and inactive lesions of destructive periodontal disease" J. Clin. Periodontol 1988: 15 pp316-323.
Slots et al "*Bacteroides gingivalis, bacteroides intermedius* and *actinobacillus actinomycetemcomitans* in human periodontal diseases" J. Clin. Periodontal 1988; 15: pp85-93.
Genco et al Host Responses in Periodontal Diseases: J. Dent. Res 63(3) Mar. 1984; pp 441-451.
International Search Report dated Dec. 24, 2002.
R. Pike, et al.; Lysine-and Arginine-specific Proteinases from *Porphyromonas gingivalis*.; J. Biol. Chem.; vol. 269; No. 1; pp. 406-411./Cited in the International Search Report.
T. Baba, et al; "Tokushu Protease to Shikkan, Shishubyo Kenkyu no Saizensen—Shishu Byogen Saikin to Shishu Byogensei Inshi wa Dokomade Akirakani saretaka"; *The Tissue Culture Engineering*; vol. 27; No. 9; Aug. 2001; pp. 343-347./Cited in the International Search Report.

*Primary Examiner*—Bruce R. Campell
*Assistant Examiner*—Satyanarayana R. Gudibande
(74) *Attorney, Agent, or Firm*—Armstrong, Kratz, Quintos, Hanson & Brooks, LLP

(57) ABSTRACT

The present invention provides a peptide derivative of formula (I) or a pharmaceutically acceptable salt thereof (I)

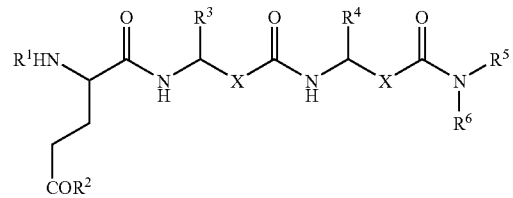

wherein X is —CH(OH)— or —CO—; $R^1$ is hydrogen or an amino protecting group; $R^2$ is hydroxyl or lower alkoxy; one of $R^3$ and $R^4$ is the side chain (R group) of lysine the amino group of which may be protected with a protecting group and the other of $R^3$ and $R^4$ is the side chain (R group) of arginine the guanidino group of which may be protected with a protecting group; and $R^5$ and $R^6$ may be the same or different and are hydrogen, lower alkyl or aralkyl. The present invention further provides a production process and use thereof.

14 Claims, No Drawings

PEPTIDE DERIVATIVE, AND PHARMACEUTICALLY ACCEPTABLE SALT THEREOF, PROCESS FOR PRODUCING THE SAME, AND USE THEREOF

TECHNICAL FIELD

The present invention relates to a novel peptide derivative and pharmaceutically acceptable salts thereof, and a production process and use thereof.

BACKGROUND ART

Most periodontal diseases are considered to be a kind of infectious disease caused by indigenous microbes residing in the periodontal area. Among such indigenous microbes, a gram-negative anaerobic bacterium called *Porphyromonas gingivalis* (hereinafter abbreviated as "*P. gingivalis*") has been revealed to be the most important pathogenic bacterium that causes adult periodontitis and rapidly progressive periodontitis (J. Clin. Periodontol., 15, 85–93, 1988; ibid 316–323, 1988; J. Dent. Res., 63, 441–451, 1984). In recent years, it has become known that proteases produced by *P. gingivalis* decompose periodontal tissue components such as collagen and blood serum proteins involved in the body's natural defense system and the proteases have revealed to be closely related to the pathogenicity of *P. gingivalis* (Greiner D., Mayrand D.: Biology of the Species *Porphyromonas Gingivalis*, Edited by Shah H. N., Mayrrand D. and Genco R. J., pp. 227–243, CRC Press, Boca Raton, Ann Arbor, London, Tokyo, 1993).

Several kinds of proteolytic enzymes having trypsin-like protease activity and produced by *P. gingivalis* are known. Among them, Lys-gingipain (hereinafter sometimes abbreviated as "KGP") and Arg-gingipain (hereinafter sometimes abbreviated as "RGP") are the principal proteolytic enzymes. These enzymes are known to have potent digestive activities to decompose high molecular weight kininogen and fibrinogen and are considered to be involved in bacterial attachment, the onset of periodontal disease and periodontal tissue destruction (J. Biol. Chem., 269, 406–411, 1994).

Conventionally, drugs for inhibiting the growth of bacteria are used to prevent and treat periodontal disease. Examples of such drugs include antibiotics such as tetracycline and minocycline; natural products such as chamomile tincture and rhatany tincture; cyclohexadine, tranexamic acid and the like. However, these drugs have safety problems or other various problems such as unpleasant smell. Japanese Unexamined Patent Publication No. 1993-97708 discloses periodontal therapeutic agents comprising an ATPase inhibitor, a cysteine protease inhibitor or the like as an active ingredient. Japanese Unexamined Patent Publications Nos. 1999-139947 and 2000-191487 disclose a composition for use in the oral cavity comprising a matrix metalloprotease inhibitor as an active ingredient. However, the anti-periodontal disease effects of the therapeutic agent and the composition are not satisfactory. Recently known inhibitors for selectively inhibiting RGP are malabaricon C described in Japanese Unexamined Patent Publication No. 1999-335274 and an arginine derivative described in Japanese Unexamined Patent Publication No. 1999-228526. A lysine derivative described in Tissue Culture Engineering, 27 (9), 343–347, 2001 is known as an inhibitor capable of selectively inhibiting KGP.

However, these publications do not describe a compound capable of inhibiting both enzymes, KGP and RGP.

DISCLOSURE OF THE INVENTION

An object of the invention is to provide a novel compound that has potent inhibitory activity against both enzymes, KGP and RGP, thus being useful as a periodontal preventive or therapeutic agent, and provide a production process thereof.

Another object of the invention is to provide a novel inhibitor capable of inhibiting both KGP and RGP, a pharmaceutical preparation for periodontal disease and a composition for use in the oral cavity.

A further object of the invention is to provide a novel method for preventing or treating periodontal disease.

Other objects and features of the invention will become apparent from the following description.

To produce an effective preventive and therapeutic agent for periodontal disease, the present inventors carried out intensive research focusing on the following points: *P. gingivalis* plays a significant role in the onset and progress of periodontal disease; and the proteolytic enzymes KGP and RGP both contribute to periodontal diseases caused by *P. gingivalis*. As a result, the inventors found a novel peptide derivative capable of potently inhibiting the enzymatic activities of both proteases, KGP and RGP. The inventors carried out further research based on the above finding and accomplished the present invention.

The present invention provides the following novel peptide derivatives having inhibitory activity against both KGP and RGP, pharmaceutically acceptable salts thereof, and production processes and uses thereof.

1. A peptide derivative of formula (I) or a pharmaceutically acceptable salt thereof

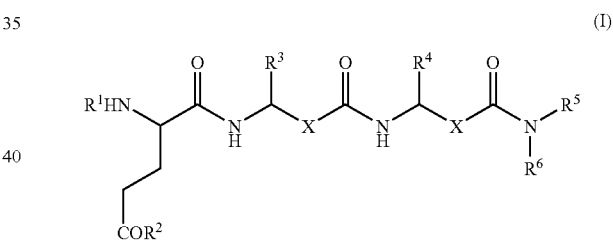

wherein X is —CH(OH)— or —CO—; $R^1$ is hydrogen or an amino protecting group; $R^2$ is hydroxyl or lower alkoxy; one of $R^3$ and $R^4$ is the side chain (R group) of lysine the amino group of which may be protected with a protecting group and the other of $R^3$ and $R^4$ is the side chain (R group) of arginine the guanidino group of which may be protected with a protecting group; and $R^5$ and $R^6$ may be the same or different and are hydrogen, lower alkyl or aralkyl.

2. The peptide derivative of formula (I) or a pharmaceutically acceptable salt thereof according to item 1 wherein X is —CO—.

3. The peptide derivative of formula (I) or a pharmaceutically acceptable salt thereof according to item 2 wherein X is —CO—; $R^1$ is hydrogen or optionally substituted aralkyloxycarbonyl; $R^2$ is hydroxyl or lower alkoxy; one of $R^3$ and $R^4$ is the side chain (R group) of lysine and the other of $R^3$ and $R^4$ is the side chain (R group) of arginine the guanidino group of which may be protected with a nitro group; and $R^5$ and $R^6$ may be the same or different and are hydrogen or aralkyl.

4. The peptide derivative of formula (I) or a pharmaceutically acceptable salt thereof according to item 3 wherein X is —CO—; $R^1$ is benzyloxycarbonyl; $R^2$ is hydroxyl or t-butoxy; $R^3$ is the side chain (R group) of lysine; $R^4$ is the side chain (R group) of arginine the guanidino group of which is protected with a nitro group; $R^5$ is hydrogen; and $R^6$ is phenethyl.

5. A process for preparing a peptide derivative of formula (I) or a pharmaceutically acceptable salt thereof

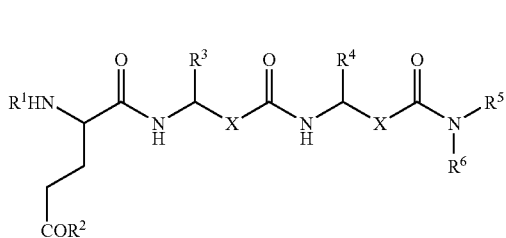

(I)

wherein X is —CH(OH)— or —CO—; $R^1$ is hydrogen or an amino protecting group; $R^2$ is hydroxyl or lower alkoxy; one of $R^3$ and $R^4$ is the side chain (R group) of lysine the amino group of which may be protected with a protecting group and the other of $R^3$ and $R^4$ is the side chain (R group) of arginine the guanidino group of which may be protected with a protecting group; and $R^5$ and $R^6$ may be the same or different and are hydrogen, lower alkyl or aralkyl, the process comprising the following step (i):

(i) condensing a compound of formula (II)

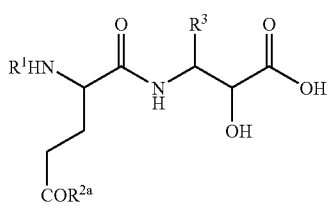

(II)

wherein $R^1$ and $R^3$ are as defined above and $R^{2a}$ is lower alkoxy, with a compound of formula (III)

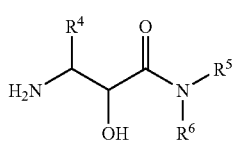

(III)

wherein $R^4$, $R^5$ and $R^6$ are as defined above to produce a peptide derivative of formula (I-a) or a pharmaceutically acceptable salt thereof

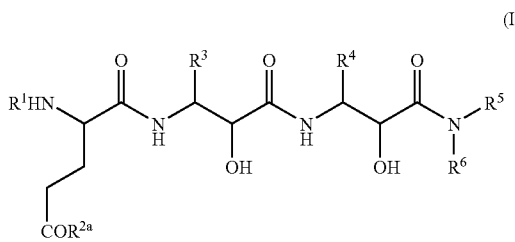

(I-a)

wherein $R^1$, $R^{2a}$, $R^3$, $R^4$, $R^5$ and $R^6$ are as defined above.

6. A process for preparing a peptide derivative of formula (I) or a pharmaceutically acceptable salt thereof, comprising the following step (ii):

(ii) oxidizing a compound of formula (I-a) to produce a peptide derivative of formula (I-b) or a pharmaceutically acceptable salt thereof

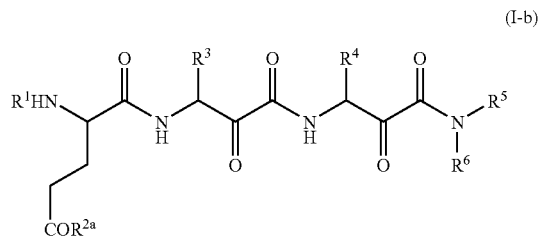

(I-b)

wherein $R^1$, $R^{2a}$, $R^3$, $R^4$, $R^5$ and $R^6$ are as defined above.

7. A process for preparing a peptide derivative of formula (I) or a pharmaceutically acceptable salt thereof, comprising the following step (iii):

(iii) treating a compound of formula (I-a) or (I-b) with an acid to produce a peptide derivative of formula (I-c) or a pharmaceutically acceptable salt thereof

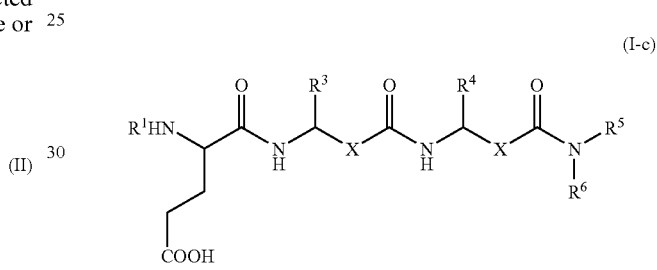

(I-c)

wherein X, $R^1$, $R^3$, $R^4$, $R^5$ and $R^6$ are as defined above.

8. An Arg-gingipain and Lys-gingipain inhibitor comprising as an active ingredient at least one member selected from the group consisting of a peptide derivative of formula (I) according to item 1 and a pharmaceutically acceptable salt thereof.

9. A pharmaceutical preparation for periodontal disease comprising as an active ingredient at least one member selected from the group consisting of a peptide derivative of formula (I) according to item 1 and a pharmaceutically acceptable salt thereof.

10. A composition for use in the oral cavity comprising a pharmaceutically acceptable carrier and at least one member selected from the group consisting of a peptide derivative of formula (I) according to item 1 and a pharmaceutically acceptable salt thereof.

11. A method of preventing periodontal disease, comprising administering an effective amount of the Arg-gingipain and Lys-gingipain inhibitor of item 8 to a mammal including a human.

12. A method of preventing periodontal disease, comprising administering an effective amount of the pharmaceutical preparation for periodontal disease of item 9 to a mammal including a human.

13. A method of preventing periodontal disease, comprising administering an effective amount of the composition for use in the oral cavity of item 10 to a mammal including a human.

14. A method of treating periodontal disease, comprising administering an effective amount of the Arg-gingipain and Lys-gingipain inhibitor of item 8 to a mammal including a human with periodontal disease.

15. A method of treating periodontal disease, comprising administering an effective amount of the pharmaceutical preparation for periodontal disease of item 9 to a mammal including a human with periodontal disease.

16. A method of treating periodontal disease, comprising administering an effective amount of the composition for use in the oral cavity of item 10 to a mammal including a human with periodontal disease.

17. Use of the peptide derivative of item 1 or a pharmaceutically acceptable salt thereof for preparing the Arg-gingipain and Lys-gingipain inhibitor of item 8.

18. Use of the peptide derivative of item 1 or a pharmaceutically acceptable salt thereof for preparing the pharmaceutical preparation for periodontal disease of item 9.

19. Use of the peptide derivative of item 1 or a pharmaceutically acceptable salt thereof for preparing the composition for use in the oral cavity of item 10.

In formula (I), the amino protecting group represented by $R^1$ is not specifically limited as long as it does not adversely affect living organisms and synthetic reactions. Commonly used amino protecting groups, such as those described in T. W. Greene, "Protective groups in Organic Synthesis", A Wiley-Interscience Publication, John-Wiley & Sons, New York, 1981, pp. 218–287, are suitable. Specific examples include optionally substituted aralkyloxycarbonyl, optionally substituted lower alkyloxycarbonyl, substituted sulfonyl, acetyl, benzyl, 1-adamantyloxycarbonyl, cyclopentyloxycarbonyl and the like.

Examples of optionally substituted aralkyloxycarbonyl groups include benzyloxycarbonyl (Cbz); benzyloxycarbonyl substituted with 1 to 3 $C_{1-4}$ lower alkoxy groups, such as p-methoxybenzyloxycarbonyl and p-ethoxybenzyloxycarbonyl; benzyloxycarbonyl substituted with a nitro group, such as p-nitrobenzyloxycarbonyl; benzyloxycarbonyl substituted with 1 to 3 halogen atoms, such as p-bromobenzyloxycarbonyl and 2,4-dichlorobenzyloxycarbonyl; diphenylmethoxycarbonyl and the like.

Examples of optionally substituted lower alkyloxycarbonyl groups include $C_{2-7}$ straight or branched chain lower alkyloxycarbonyl optionally substituted with 1 to 3 halogen atoms, such as methoxycarbonyl, ethoxycarbonyl, t-butoxycarbonyl (Boc), 9-fluorenylmethyloxycarbonyl and 2,2,2-trichloroethyloxycarbonyl.

Examples of the substituted sulfonyl group include sulfonyl having one substituent such as a $C_{1-6}$ straight or branched chain lower alkyl group or a phenyl group optionally substituted with 1 to 3 $C_{1-6}$ straight or branched chain lower alkyl groups, such as benzenesulfonyl, p-toluenesulfonyl and methanesulfonyl.

Preferably, the amino protecting group represented by $R^1$ is an optionally substituted aralkyloxycarbonyl group or an optionally substituted lower alkyloxycarbonyl group. Especially preferable is optionally lower alkoxy-, nitro- or halogen-substituted benzyloxycarbonyl, or optionally halogen-substituted $C_{2-7}$ straight or branched chain lower alkyloxycarbonyl. Particularly preferable is benzyloxycarbonyl or 2,2,2-trichloroethyloxycarbonyl.

Examples of lower alkoxy groups represented by $R^2$ include $C_{1-6}$ straight or branched chain lower alkoxy groups such as methoxy, ethoxy, n-propoxy, isopropoxy, n-butoxy, isobutoxy and t-butoxy. Preferable is t-butoxy.

The side chain (R group) of lysine represented by $R^3$ or $R^4$ means the side chain or residue bonded to the α-carbon atom of lysine, i.e., 4-aminobutyl. The amino group of the side chain (R group) may be protected with a protecting group.

Examples of useful amino protecting groups are the above-mentioned amino protecting groups. Preferably, the amino protecting group is a $C_{2-7}$ straight or branched chain lower alkyloxycarbonyl group optionally substituted with 1 to 3 halogen atoms. Especially preferable are unsubstituted $C_{2-7}$ straight or branched chain lower alkyloxycarbonyl groups. Particularly preferable is t-butoxycarbonyl.

The side chain (R group) of arginine means the side chain or residue bonded to the α-carbon atom of arginine, i.e., 3-guanidinopropyl. The guanidino group of the side chain (R group) may be protected with a protecting group. The protecting group is not specifically limited as long as it does not adversely affect living organisms and synthetic reactions. Commonly used guanidino protecting groups, such as those described in T. W. Greene, "Protective groups in Organic Synthesis", A Wiley-Interscience Publication, John-Wiley & Sons, New York, 1981, pp. 218–287, are suitable for use. Specific examples include nitro; sulfonyl substituted with one substituent such as phenyl optionally substituted with 1 to 3 $C_{1-6}$ straight or branched chain lower alkyl groups, or chromane optionally substituted with 1 to 6 $C_{1-6}$ straight or branched chain lower alkyl groups, such as p-toluenesulfonyl and 2,2,5,7,8-pentamethylchromane-6-sulfonyl; and oxycarbonyl groups substituted with one substituent such as aralkyl or adamantyl, such as benzyloxycarbonyl, phenethyloxycarbonyl and 1-adamantyloxycarbonyl. Preferable is nitro.

Examples of lower alkyl groups represented by $R^5$ and $R^6$ are $C_{1-6}$ straight or branched chain lower alkyl groups such as methyl, ethyl, n-propyl, isopropyl, n-butyl, isobutyl, s-butyl, t-butyl, n-pentyl, isopentyl, 1-ethylpropyl, n-hexyl, isohexyl, 1-ethylbutyl and the like. Preferable are methyl and ethyl.

Examples of aralkyl groups include phenyl-$C_1$–$C_6$ alkyl, particularly benzyl and phenethyl.

Of the compounds of formula (I), preferable are those wherein X is —CO—. Especially preferable are those wherein X is —CO—, $R^1$ is hydrogen or optionally substituted aralkyloxycarbonyl, $R^2$ is hydroxyl or $C_{1-6}$ straight or branched chain lower alkoxy, one of $R^3$ and $R^4$ is the side chain (R group) of lysine and the other of $R^3$ and $R^4$ is the side chain (R group) of arginine the guanidino group of which may be protected with a nitro group, and $R^5$ and $R^6$ may be the same or different and are hydrogen or aralkyl. Particularly preferable compounds are those wherein X is —CO—, $R^1$ is benzyloxycarbonyl, $R^2$ is hydroxyl or t-butoxy, $R^3$ is the side chain (R group) of lysine, $R^4$ is the side chain (R group) of arginine the guanidino group of which is protected with a nitro group, $R^5$ is hydrogen and $R^6$ is phenethyl.

The pharmaceutically acceptable salts of the compounds of the invention are not particularly limited. Examples thereof include acid addition salts formed by reacting the compounds of the invention with pharmaceutically acceptable acids. Specific examples include inorganic acid salts such as hydrochlorides and sulfates; and organic acid salts such as formates, trifluoroacetates, acetates, tartrates, maleates, fumarates, succinates and methanesulfonates. The compounds of the invention or pharmaceutically acceptable salts thereof may be in the form of solvates such as hydrates.

The amino acids constituting the compound of the invention may be L- or D-amino acids. Preferable are L-amino acids.

The compounds of the invention may exist as enantiomers or diastereoisomers depending on the asymmetric carbons in the molecular structure. All such enantiomers and diastereoisomers are included in the scope of the invention. Such compounds can be used as is as isomeric mixtures or can be optically resolved by conventional techniques.

The compounds of formula (I) can be prepared according to the following reaction schemes.

[Reaction Scheme 1]

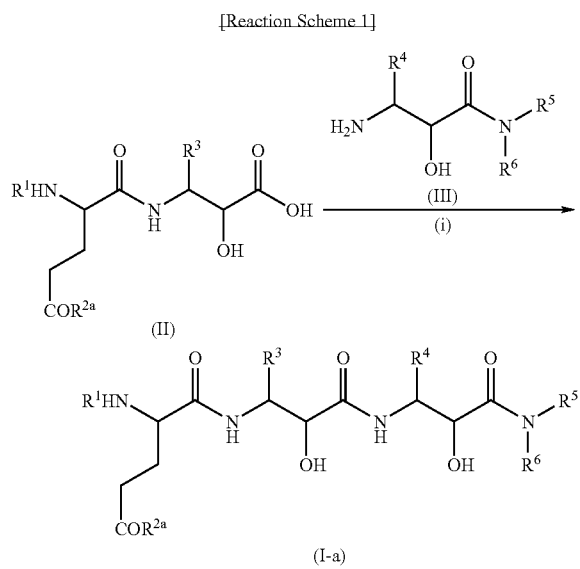

wherein $R^1$, $R^3$, $R^4$, $R^5$ and $R^6$ are as defined above; and $R^{2a}$ is lower alkoxy.

Examples of lower alkoxy groups represented by $R^{2a}$ include $C_{1-6}$ straight or branched chain lower alkoxy groups, preferably methoxy, ethoxy and t-butoxy.

Step (i): The compound of formula (I-a) of the invention can be synthesized by condensing a compound of formula (II) with a known compound of formula (III) prepared according to the method described in Japanese Unexamined Patent Publication No. 1999-228526 in a suitable solvent.

The condensation reaction can be carried out by conventional methods. Useful methods include, for example, methods using a condensing agent such as N,N-dicyclohexylcarbodiimide, 1-ethyl-3-(3-dimethylaminopropyl)carbodiimide hydrochloride or the like; methods using additives (e.g., 1-hydroxybenzotriazole, N-hydroxy-5-norbornene-2,3-dicarboxyimide, etc.) in addition to the condensing agent; mixed acid anhydride methods using isobutyl chloroformate, etc.; azide methods; active ester methods; and the like.

Any solvent can be used in the condensation reaction so long as it is inert to the reaction. Useful solvents include, for example, N,N-dimethylformamide, tetrahydrofuran, methylene chloride, dioxane, ethyl acetate, N-methylpyrrolidone and the like. These solvents can be used singly or in combination of two or more. The amount of compound of formula (III) is about 0.5 to about 10 moles, and preferably about 1 to about 5 moles, per mole of the compound of formula (II). The amount of condensing agent is about 0.5 to about 10 moles, preferably about 1 to about 5 moles, per mole of compound of formula (II). The reaction time is about 0.3 to about 100 hours, and preferably about 0.5 to about 20 hours. The reaction temperature is about −20° C. to about 100° C., and preferably 0° C. to about 40° C. The compound obtained in this step can be used in the following reaction step, with or without being isolated.

[Reaction Scheme 2]

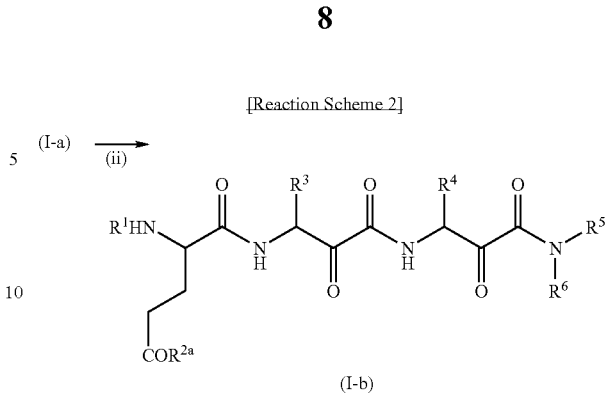

wherein $R^1$, $R^{2a}$, $R^3$, $R^4$, $R^5$ and $R^6$ are as defined above.

Step (ii): The compound of formula (I-b) of the invention can be synthesized by oxidizing the compound of formula (I-a) obtained in Reaction Scheme 1 in a suitable solvent.

The oxidation reaction can be carried out by conventional methods. Useful methods include, for example, Dess-Martin oxidation using Dess-Martin reagents; improved Moffat oxidation using dimethyl sulfoxide/1-ethyl-3-(3-dimethylaminopropyl)carbodiimide hydrochloride/dichloroacetic acid; and oxidation using N-tert-butylphenylsulfinimidoyl chloride.

Any solvent can be used in the oxidation reaction so long as it is inert to the reaction. Useful solvents include, for example, N,N-dimethylformamide, tetrahydrofuran, methylene chloride, dioxane, ethyl acetate, acetonitrile, N-methylpyrrolidone and the like. These solvents can be used singly or in combination of two or more. The amount of oxidizing reagent is about 0.3 to about 100 moles, preferably about 1 to about 10 moles, per mole of compound of formula (I-a). The reaction time is about 0.1 to about 100 hours, preferably about 0.5 to about 50 hours. The reaction temperature is about −78° C. to about 100° C., and preferably about 0° C. to about 40° C. The compound obtained in this step can be used in the following reaction step, with or without being isolated.

[Reaction Scheme 3]

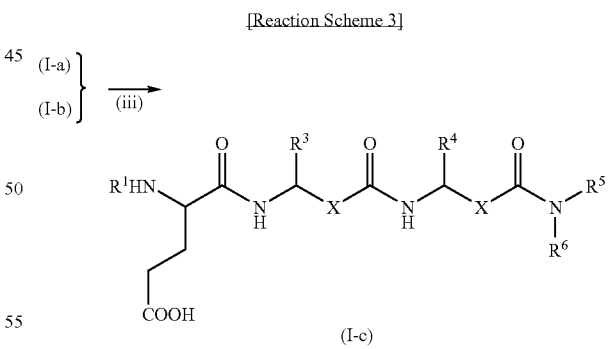

wherein X, $R^1$, $R^3$, $R^4$, $R^5$ and $R^6$ are as defined above.

Step (iii): The compound of formula (I-c) of the invention can be obtained by treating a compound of formula (I-a) or (I-b) obtained in Reaction Scheme 1 or 2 with an acid, in a suitable solvent or in the absence of solvents.

Any solvent can be used in the reaction as long as it is inert to the reaction. Useful solvents include, for example, chloroform, methylene chloride, dioxane, tetrahydrofuran and ethyl acetate. Useful acids include, for example, mineral acids such as hydrochloric acid and sulfuric acid; and organic acids such as trifluoroacetic acid and p-toluenesulfonic acid. The amount of acid used in the reaction is about 1 to about 1,000 moles, and preferably about 1 to about 100 moles, per mole of the compound of formula (I-a) or (I-b). The reaction time is about 0.5 to about 50 hours. The reaction temperature is about 0° C. to about 100° C., and preferably about 0° C. to about 30° C.

The compound of formula (II) can be produced, for example, according to the following Reaction Scheme 4:

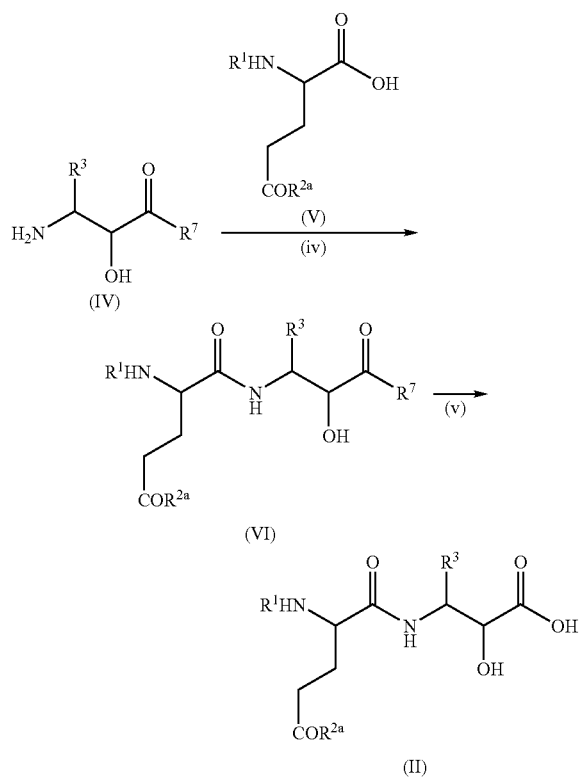

wherein $R^1$, $R^{2a}$ and $R^3$ are as defined above and $R^7$ is lower alkoxy.

Examples of lower alkoxy groups represented by $R^7$ include the above-mentioned $C_{1-6}$ straight or branched chain lower alkoxy groups. Preferable are methoxy, ethoxy and t-butoxy.

Step (iv): The compound of formula (VI) of the invention can be produced by condensing a compound of formula (IV) with a known compound of formula (V) in a suitable solvent.

The condensation reaction can be carried out by conventional methods. Useful methods include, for example, methods using a condensing agent such as N,N-dicyclohexylcarbodiimide, 1-ethyl-3-(3-dimethylaminopropyl)carbodiimide hydrochloride or the like; methods using additives (e.g., 1-hydroxybenzotriazole, N-hydroxy-5-norbornene-2,3-dicarboxyimide, etc.) in addition to the condensing agent; mixed acid anhydride methods using isobutyl chloroformate, etc.; azide methods; and active ester methods.

Any solvent can be used in the condensation reaction so long as it is inert to the reaction. Useful solvents include, for example, N,N-dimethylformamide, tetrahydrofuran, methylene chloride, dioxane, ethyl acetate, N-methylpyrrolidone and the like. These solvents can be used singly or in combinations of two or more. The amount of compound of formula (V) is about 0.5 to about 10 moles, preferably about 1 to about 5 moles, per mole of compound of formula (IV). The amount of condensing agent is about 0.5 to about 10 moles, preferably about 1 to about 5 moles, per mole of compound of formula (IV). The reaction time is about 0.3 to about 100 hours, and preferably about 0.5 to about 20 hours. The reaction temperature is about −10° C. to about 100° C., and preferably about 0° C. to about 40° C. The compound obtained in this step can be used in the following reaction step (v), with or without being isolated.

The compound of formula (IV) can be obtained by subjecting a known compound described in WIPO Publication No. WO 98/50420, Japanese Unexamined Patent Publication No. 1999-228526, etc. to a conventional amino group deprotection reaction. Useful deprotection reactions include, for example, catalytic hydrogenation, methods using trimethylsilyliodide or triethylsilane, and the like. Catalysts usable in catalytic reduction methods include, for example, palladium-carbon, palladium chloride and the like. Since deprotection conditions vary depending on the type of protecting group of the precursor compound, the compound of formula (IV) may be obtained in the free state or as a salt. Such salts are not particularly limited so long as they do not participate in the condensation reaction. Specific examples thereof include mineral acid salts such as hydrochlorides and sulfates; and organic acid salts such as p-toluenesulfonates and methanesulfonates.

Step (v): The compound of formula (II) can be obtained by hydrolysis of the compound (VI) obtained in the above step (iv) with a base in a suitable solvent. Any solvent can be used in the reaction so long as it is inert to the reaction. For example, water, methanol, ethanol, 1-propanol, 2-propanol, tetrahydrofuran and the like can be used singly or in combination of two or more. Examples of useful bases include lithium hydroxide, sodium hydroxide, potassium hydroxide and the like. The amount of base is about 1 to about 10 moles, and preferably about 1 to about 2 moles, per mole of the compound of formula (VI). The reaction time is about 0.3 to about 100 hours, and preferably about 0.5 to about 20 hours. The reaction temperature is about 0 to about 100° C., and preferably about 0 to about 40° C. The compound obtained in this step can be used in Reaction Scheme 1, with or without being isolated.

The compounds of the invention obtained by the above processes and the other above-mentioned compounds can be purified by the separation and purification techniques typically used in the field of chemical synthesis, such as recrystallization, distillation and various column chromatographic techniques.

The peptide derivative of formula (I) of the invention and pharmaceutically acceptable salts thereof potently inhibit KGP and RGP, proteolytic enzymes produced by *P. gingivalis* closely associated with the onset and progress of periodontal disease. The peptide derivative of the invention is composed of highly safe natural amino acids or derivatives thereof. Therefore, the peptide derivative and its metabolites produced in vivo are assumed to be highly safe.

Therefore, the peptide derivative of formula (I) and pharmaceutically acceptable salts thereof are useful as an active ingredient of Lys-gingipain and Arg-gingipain inhibitors and pharmaceutical preparations for periodontal disease. Such Lys-gingipain and Arg-gingipain inhibitors and pharmaceutical preparations for periodontal disease can be used as periodontal preventive agents and therapeutic agents.

The peptide derivative of formula (I) and pharmaceutically acceptable salts thereof can also be used, together with a pharmaceutically acceptable carrier, to prepare compositions for use in the oral cavity. The peptide derivative of the invention or pharmaceutically acceptable salts thereof can be mixed with a pharmaceutically acceptable carrier and administered as preparations for use in the oral cavity, such as gel preparations for use in the oral cavity, oral ointments for adhesive application to mucous membranes, oral pastes, periodontal-pocket intercalating agents, and preparations for adhesive application to gingivae; and oral hygiene agents such as dentifrices, mouthwashes, chewing gums, tablets, candies, troches and the like. The compositions for oral cavity can be used as periodontal preventive agents or therapeutic agents.

Useful pharmaceutically acceptable carriers include appropriate carriers commonly used in accordance with the dosage form. Specific examples include methylcellulose, hydroxymethylcellulose, hydroxyethylcellulose, carboxymethylcellulose sodium, hydroxypropylmethylcellulose, liquid paraffin, white petrolatum, platinum base, Eudragit L, sodium alginate, propylene glycol alginate, pullulan, tragacanth, xanthan gum, chitosan, polyvinylpyrrolidone, polyvinyl alcohol, polyacrylic acid, sodium polyacrylate, polymethacrylic acid, ethyl methacrylate, dimethylamino acetate, cellulose acetate, collagen, atherocollagen, gelatin, glycerol, triacetin, Macrogol 400, Polysorbate 60, polyoxyl stearate 40, butyl p-hydroxybenzoate, ethanol, cetyl alcohol, glyceryl monostearate, calcium carbonate, magnesium carbonate, calcium secondary phosphate, carrageenan, sodium dioctyl sulfosuccinate, sodium lauryl sulfate, sodium dodecylbenzenesulfonate, hinokitiol, allantoin, glycyrrhizin, gum arabic, starch, cornstarch, saccharin, saccharin sodium, stevioside, glucose, lactose, sorbitol, mannitol, magnesium stearate, monobasic potassium phosphate, dibasic potassium phosphate, menthol, eucalyptus oil, peppermint, spearmint, colors, aromas, sodium fluoride, sodium monofluorophosphate and like fluorides, lysozyme chloride, azulene and like anti-inflammatory agents, and sodium chloride and like typically added components.

When the Lys-gingipain and Arg-gingipain inhibitor, pharmaceutical preparation for periodontal disease or composition for use in oral cavity, each containing the peptide derivative of the invention or a pharmaceutically acceptable salt thereof as an active ingredient, is administered to a mammal, including a human, usable administration methods are such that the preparation is inserted, applied or used for washing in a suitable amount at least once a day with an active ingredient content of about 0.001 wt. % or more, and preferably about 0.01 to about 20 wt. %.

When the Lys-gingipain and Arg-gingipain inhibitor, pharmaceutical preparation for periodontal disease or composition for use in the oral cavity of the invention is used as a therapeutic agent, the dosage can be suitably selected according to the mode of administration, the age, gender and other conditions of the patient, and the severity of disease. When administered to a human, the dosage of the active ingredient compound of the invention is usually about 0.001 to about 100 mg per kg body weight per day, and preferably about 0.005 to about 10 mg/kg/day.

When the Lys-gingipain and Arg-gingipain inhibitor, pharmaceutical preparation for periodontal disease or composition for oral cavity of the invention is used as preventive agents, the dosage can be suitably selected according to the mode of administration, the age, gender and other conditions of the human or other mammal. When administered to a human, the dosage of the active ingredient compound of the invention is usually about 0.001 to about 100 mg per kg body weight per day, preferably about 0.005 to about 10 mg/kg/day.

BEST MODE FOR CARRYING OUT THE INVENTION

The following Reference Examples, Examples, Formulation Examples and Test Examples are provided to illustrate the invention in more detail. It is to be understood that the invention is not limited to the Examples. In the examples, Me represents methyl; Boc, t-butoxycarbonyl; Cbz, benzyloxycarbonyl; t-Bu, t-butyl; and Ph, phenyl. Abbreviations for amino acids follow the generally used recommendations of the IUPAC-IUB.

REFERENCE EXAMPLE 1

The following compound, included in the compound of formula (VI) shown in Reaction Scheme 4, was synthesized.

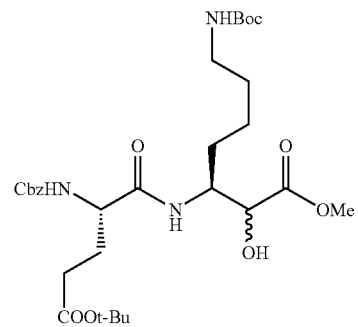

Four grams of 10% palladium-carbon was added to 1,000 ml of a mixed methanol/chloroform (10:1) solution containing 21 g (49.5 mmol) of methyl (3S)-3-benzyloxycarbonylamino-7-tert-butoxycarbonylamino-2-hydroxyheptanoate (Cbz-Lys(Boc)ψ[CHOHCO]-OMe), i.e., a known compound prepared according to the method described in WO 98/50420. The resulting mixture was stirred under a hydrogen atmosphere at room temperature for 3 hours and 45 minutes to eliminate the benzyloxycarbonyl protecting group from the amino group of lysine. After completion of the reaction, insoluble matter was filtered off. The filtrate was concentrated and then, without isolation and purification, dissolved in 525 ml of N,N-dimethylformamide (DMF). Twenty grams (59.4 mmol) of N-benzyloxycarbonyl-L-glutamic acid γ-t-butylester (Cbz-Glu(O-t-Bu)-OH), 8.7 g (64.3 mmol) of 1-hydroxybenzotriazole, 11.4 g (59.4 mmol) of 1-ethyl-3-(3-dimethylaminopropyl)carbodiimide hydrochloride and 13.5 g (134 mmol) of N-methylmorpholine were added to this solution with ice-cooling, and the mixture was stirred at room temperature for 14 hours. After completion of the reaction, a 10% aqueous citric acid solution was added to adjust the pH to 3 and the reaction mixture was extracted with ethyl acetate. The ethyl acetate layer was washed sequentially with a saturated saline solution, a 5% aqueous sodium hydrogen carbonate solution and a saturated saline solution, and dried over anhydrous sodium sulfate. After filtration, the solvent was distilled off and the residue was separated and purified by silica gel column chromatography (hexane:ethyl acetate=3:2 to 1:1), giving 18.3 g of a diastereomeric mixture of the desired compound as a white powder (yield: 60%). The following are the physical properties of the mixture.

$^1$H-NMR(DMSO-$d_6$)δ: 7.67 (0.3H, d, J=8.8 Hz), 7.54 (0.7H, d, J=9.0 Hz), 7.40–7.25 (6H, m), 6.73 (1H, m), 5.69 (0.3H, d, J=5.9 Hz), 5.53 (0.7H, d, J=5.6 Hz), 5.02 (2H, m), 4.11–3.96 (3H, m), 3.61 & 3.56 (3H, s), 2.87 (2H, m), 2.20 (2H, m), 1.83 (1H, m), 1.66 (1H, m), 1.59–1.06 (6H, m), 1.38 (9H, s), 1.36 (9H, s)

Mass (FAB(+)): 610 (M+H)$^+$

State: white powder m.p.: 101 to 103° C.

REFERENCE EXAMPLE 2

The following compound, included in the compound of formula (II) shown in Reaction Scheme 4, was synthesized.

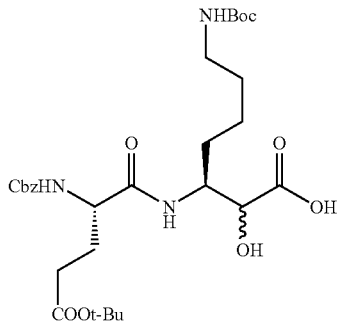

An aqueous solution (10 ml) of 270 mg (6.43 mmol) of lithium hydroxide monohydrate was added to 100 ml of a tetrahydrofuran (THF) solution of 3.53 g (5.76 mmol) of the compound obtained in Reference Example 1 with ice cooling. The resulting mixture was stirred with ice-cooling for 1 hour and at room temperature for 30 minutes. After completion of the reaction, the reaction mixture was concentrated under reduced pressure. A 10% aqueous solution of citric acid was added to the residue to adjust the pH to 3, followed by extraction with ethyl acetate. The ethyl acetate layer was washed with a saturated saline solution and then dried over anhydrous sodium sulfate. After filtration, the solvent was distilled off, giving 3.5 g of the desired compound as a white powder (yield: 100%). The following are the physical properties of the compound.

$^1$H-NMR(DMSO-d$_6$)δ: 12.45 (1H, br s), 7.49–7.31 (7H, m), 6.74 (1H, m), 5.38 (0.3H, d, J=5.8 Hz), 5.26 (0.7H, d, J=5.8 Hz), 5.01 (1H, q, J=12.4 Hz), 4.04–3.85 (4H, m), 2.86 (2H, m), 2.19 (2H, m), 1.90–0.90 (8H, m), 1.40–1.36 (18H, s×2)

Mass (FAB(-)): 596 (M+H)$^+$, 594 (M-H)$^-$

State: white powder m.p.: 48 to 50° C.

EXAMPLE 1

The following compound of the invention was synthesized.

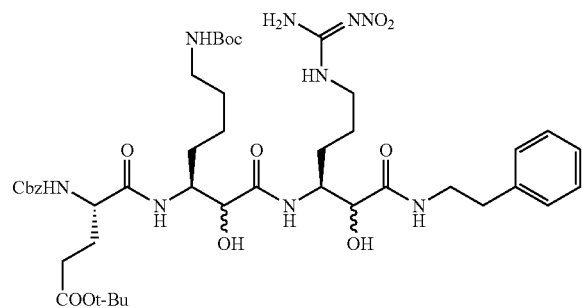

One hundred and seventy two milligrams (0.44 mmol) of hydrochloride salt of 6-nitroguanidino-(3S)-amino-2-hydroxyheptanoic acid N-phenethylamide (H-Arg(N$^g$NO$_2$)—CH(OH)—CONHCH$_2$CH$_2$Ph) described in Japanese Unexamined Patent Publication No. 1996-502493, 63 mg (0.46 mmol) of 1-hydroxybenzotriazole, 89 mg (0.46 mmol) of 1-ethyl-3-(3-dimethylaminopropyl)carbodiimide hydrochloride and 89 mg (0.88 mmol) of N-methylmorpholine were added to 4 ml of a DMF solution of 263 mg (0.44 mmol) of the compound obtained in Reference Example 2 with ice-cooling, and the resulting mixture was stirred at room temperature for 3.5 hours. After completion of the reaction, a 10% aqueous citric acid solution was added to adjust the pH to 3, followed by extraction with ethyl acetate. The ethyl acetate layer was washed sequentially with a saturated saline solution, a 5% aqueous sodium hydrogen carbonate solution and a saturated saline solution, and dried over anhydrous sodium sulfate. After filtration, the solvent was distilled off and the residue was separated and purified by silica gel column chromatography (chloroform:methanol=20:1), giving 190 mg of a diastereomeric mixture of the desired compound as an amorphous solid (yield: 46%). The following are the physical properties of the mixture.

$^1$H-NMR(DMSO-d$_6$)δ: 8.50 (0.5H, m), 8.25–7.17 (14.5H, m), 6.75–6.58(1H, m), 6.01–5.75 (2H, m), 4.99 (2H, m), 4.25–3.82 (5H, m), 3.48–2.97(4H, m), 2.91–2.65 (4H, m), 2.20 (2H, m), 1.95–1.58 (2H, m), 1.52–1.11 (28H, m)

Mass(FAB(+)); 952 (M+Na)$^+$, 968 (M+K)$^+$

State: amorphous

EXAMPLE 2

The following compound of the invention was synthesized.

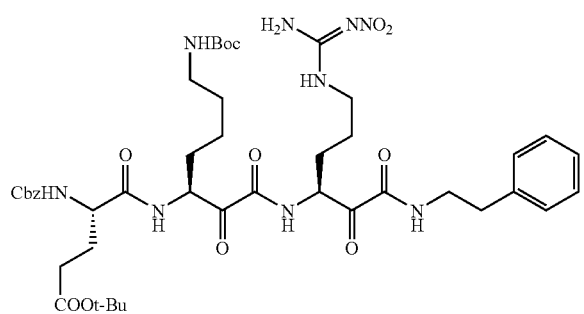

One hundred and forty four milligrams (0.34 mmol) of Dess-Martin reagent was added to 2 ml of a methylene chloride solution of 105 mg (0.11 mmol) of the compound obtained in Example 1, and the mixture was stirred at room temperature for 1 hour. After completion of the reaction, a 20% aqueous sodium hydrogen sulfite solution was added. The mixture was stirred for 5 minutes and extracted with ethyl acetate. The ethyl acetate layer was washed sequentially with a saturated saline solution, a 5% aqueous sodium hydrogen carbonate solution and a saturated saline solution, and then dried over anhydrous sodium sulfate. After filtration, the solvent was distilled off, and the residue was separated and purified by silica gel column chromatography (chloroform:methanol=40:1), giving 101 mg of the desired compound as an amorphous solid (yield: 97%). The following are the physical properties of the compound.

$^1$H-NMR(DMSO-d$_6$)δ: 9.10–8.00 (3H, m), 7.55–7.15 (12H, m), 6.80–6.62 (1H, m), 5.06–4.94 (3H, m), 4.18–3.91 (2H, m), 3.21–2.65 (8H, m), 2.29–2.18 (2H, m), 1.86–0.98 (30H, m)

LC/Mass ES(+); 925 (M$^+$), ES(−); 924 (M−H)$^−$
State: amorphous

EXAMPLE 3

The following compound of the invention was synthesized.

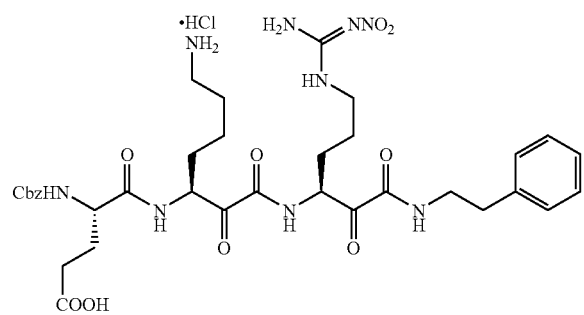

Two milliliters of a 4N hydrochloric acid-ethyl acetate solution was added to 75 mg (0.08 mmol) of the compound obtained in Example 2, and the mixture was stirred at room temperature for 40 minutes. Anhydrous ether was added to the reaction mixture and the resulting white precipitate was collected by filtration and washed with anhydrous ether, giving 59 mg of the desired compound as an amorphous solid (yield: 90%). The following are the physical properties of the compound.

$^1$H-NMR(DMSO-d$_6$)δ: 9.10–8.30 (3H, m), 7.75 (3H, br s), 7.60–7.11 (12H, m), 6.80–6.60 (1H, m), 5.06–4.95 (3H, m), 4.20–3.95 (2H, m), 3.20–2.61 (8H, m), 2.31–2.18 (2H, m), 1.86–1.00 (12H, m)

Mass(FAB(+)); 770 (M+H)$^+$, 768 (M−H)$^−$
State: amorphous

| Formulation Example 1 Oral ointment | |
|---|---|
| Compound 1 of the invention obtained in Example 1 | 1.0 |
| White petrolatum | 10.0 |
| Sodium polyacrylate | 3.0 |
| Liquid paraffin | Balance |
| Total | 100.0 (wt. %) |

An oral ointment was prepared in a conventional manner according to the above formulation.

| Formulation Example 2 Dentifrice | |
|---|---|
| Calcium secondary phosphate | 42.0 |
| Glycerin | 19.0 |
| Carrageenan | 0.9 |
| Sodium lauryl sulfate | 1.2 |
| Saccharin | 1.0 |
| Compound of the invention obtained in Example 2 | 1.0 |
| Butyl p-hydroxybenzoate | 0.005 |
| Flavor | 1.0 |
| Water | Balance |
| Total | 100.0 (wt. %) |

A dentifrice was prepared in a conventional manner according to the above formulation.

| Formulation Example 3 Troche | |
|---|---|
| Gum arabic | 6.0 |
| Glucose | 72.0 |
| Lactose | 19.0 |
| Compound of the invention obtained in Example 3 | 1.5 |
| Sodium monofluorophosphate | 0.7 |
| Flavor | 1.0 |
| Water | Balance |
| Total | 100.0 (wt. %) |

Troches were prepared in a conventional manner according to the above formulation.

| Formulation Example 4 Chewing gum | |
|---|---|
| Polyvinyl acetate | 20.0 |
| Polyisobutylene | 3.0 |
| Calcium carbonate | 2.0 |
| Sorbitol | 55.0 |
| Mannitol | 15.0 |
| Compound of the invention obtained in Example 3 | 4.0 |
| Flavor | 1.0 |
| Total | 100.0 (wt. %) |

Chewing gum was prepared in a conventional manner according to the above formulation.

| Formulation Example 5 Gargle | |
|---|---|
| Ethanol | 20.0 |
| Polyoxyethylene (60) hydrogenated castor oil | 3.0 |
| Polyethylene glycol | 2.0 |
| Glycerin | 10.0 |
| Sodium saccharin | 0.02 |
| Compound of the invention obtained in Example 3 | 0.5 |
| Flavor | 0.2 |
| Water | Balance |
| Total | 100.0 (wt. %) |

A gargle was prepared in a conventional manner according to the above formulation.

| Formulation Example 6 Mouthwash | |
|---|---|
| Ethanol | 30.0 |
| Polyoxyethylene (20) sorbitan laurate | 1.0 |
| Polyoxyethylene (40) hydrogenated castor oil | 0.5 |
| Sodium hydroxide | 0.05 |
| Sodium saccharin | 0.05 |
| Compound of the invention obtained in Example 3 | 0.5 |
| Flavor | 0.5 |
| Water | Balance |
| Total | 100.0 (wt. %) |

A mouthwash was prepared in a conventional manner according to the above formulation.

TEST EXAMPLE 1

Determination of Inhibitory Activities Against KGP and RGP

The inhibitory activity against Lys-gingipain (KGP) was measured by the method of Abe et al. (Journal Biochemistry, 1998, Vol. 123, 305–312) using Cbz-His-Glu-Lys-MCA as a substrate. The inhibitory activity against Arg-gingipain (RGP) was measured by the method of Kadowaki et al. (Journal Biological Chemistry, 1994, Vol. 269, 21371–21378) using Cbz-Phe-Arg-MCA as a substrate. More specifically, the measurements were carried out in the following manner: 100 μl of 50 mM L-cystein, 200 μl of a 0.1 M sodium phosphate buffer solution (pH 7.5), 20 μl of 12.3 nM KGP or RGP solution containing 0.05% "Brij35" (a tradename, product of Aldrich, polyoxyethylene(23) lauryl ether), 80 μl of distilled water and 100 μl of a dimethyl sulfoxide solution of a compound according to the invention were mixed and preincubated at 37° C. for 5 minutes. Thereafter, 500 μl of a 0.1% dimethyl sulfoxide solution containing 20 μM Cbz-His-Glu-Lys-MCA (for KGP) or Cbz-Phe-Arg-MCA (for RGP) was added, followed by incubation at 40° C. for 10 minutes. An acetic acid buffer solution (pH 5.0) containing 10 mM iodoacetamide was then added to stop the enzyme reaction. The fluorescence intensity (F) at 460 nm upon excitation at 380 nm was measured. As a control, 100 μl of dimethyl sulfoxide that did not contain a compound according to the invention was used in place of a solution of the compound, and the fluorescence intensity ($F_0$) was measured in a manner similar to the above. The enzyme inhibitory activity was calculated by the following equation:

Enzyme inhibitory activity (%)=[1−(F/$F_0$)]×100

Table 1 shows the test results.

TABLE 1

| Compound (Example No.) | Concentration (mol/l) | Enzyme inhibitory activity (%) | |
|---|---|---|---|
| | | KGP | RGP |
| 3 | $10^{-4}$ | 100.0 | 99.4 |
| | $10^{-5}$ | 99.9 | 96.8 |
| | $10^{-6}$ | 99.9 | 81.1 |

Table 1 shows that the compound of the invention has excellent inhibitory activities against both enzymes, KGP and RGP.

The compound of the invention inhibits both Lys-gingipain (KGP) and Arg-gingipain (RGP) produced by a gram-negative anaerobic bacterium, *Porphyromonas gingivalis*, and is therefore useful, for example, as a preventive or therapeutic agent for periodontal disease.

The invention claimed is:

1. A peptide derivative of formula (I) or a pharmaceutically acceptable salt thereof

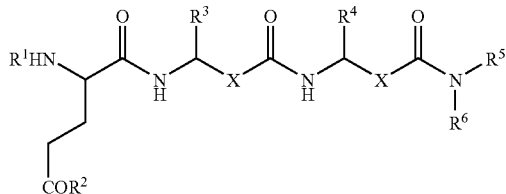

(I)

wherein X is —CH(OH)— or —CO—; $R^1$ is hydrogen or an amino protecting group; $R^2$ is hydroxyl or lower alkoxy; one of $R^3$ and $R^4$ is the side chain (R group) of lysine the amino group of which may be protected with a protecting group and the other of $R^3$ and $R^4$ is the side chain (R group) of arginine the guanidino group of which may be protected with a protecting group; and $R^5$ and $R^6$ may be the same or different and are hydrogen, lower alkyl or aralkyl.

2. The peptide derivative of formula (I) or a pharmaceutically acceptable salt thereof according to claim 1 wherein X is —CO—.

3. The peptide derivative of formula (I) or a pharmaceutically acceptable salt thereof according to claim 2 wherein X is —CO—; $R^1$ is hydrogen or optionally substituted aralkyloxycarbonyl; $R^2$ is hydroxyl or lower alkoxy; one of $R^3$ and $R^4$ is the side chain (R group) of lysine and the other of $R^3$ and $R^4$ is the side chain (R group) of arginine the guanidino group of which may be protected with a nitro group; and $R^5$ and $R^6$ may be the same or different and are hydrogen or aralkyl.

4. The peptide derivative of formula (I) or a pharmaceutically acceptable salt thereof according to claim 3 wherein X is —CO—; $R^1$ is benzyloxycarbonyl; $R^2$ is hydroxyl or t-butoxy; $R^3$ is the side chain (R group) of lysine; $R^4$ is the side chain (R group) of arginine the guanidino group of which is protected with a nitro group; $R^5$ is hydrogen; and $R^6$ is phenethyl.

5. A process for preparing a peptide derivative of formula (I) or a pharmaceutically acceptable salt thereof

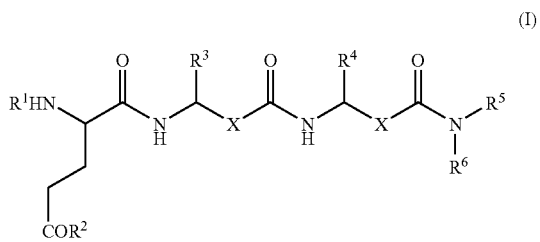

(I)

wherein X is —CH(OH)— or —CO—; $R^1$ is hydrogen or an amino protecting group; $R^2$ is hydroxyl or lower alkoxy; one of $R^3$ and $R^4$ is the side chain (R group) of lysine the amino group of which may be protected with a protecting group and the other of $R^3$ and $R^4$ is the side chain (R group) of arginine the guanidino group of which may be protected with a protecting group; and $R^5$ and $R^6$ may be the same or different and are hydrogen, lower alkyl or aralkyl, the process comprising the following step (i):
(i) condensing a compound of formula (II)

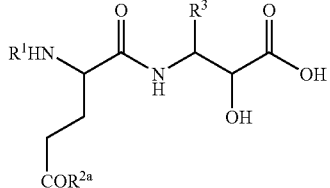
(II)

wherein $R^1$ and $R^3$ are as defined above and $R^{2a}$ is lower alkoxy, with a compound of formula (III)

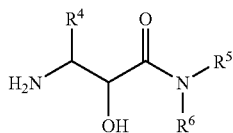
(III)

wherein $R^4$, $R^5$, and $R^6$ are as defined above to produce a peptide derivative of formula (I-a) or a pharmacuetically acceptable salt thereof

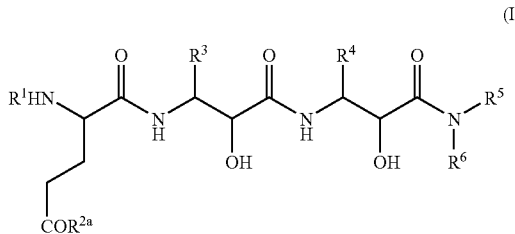
(I-a)

wherein $R^1$, $R^{2a}$, $R^3$, $R^4$, $R^5$ and $R^6$ are as defined above.

6. A process according to claim 5 for preparing a peptide derivative of formula (I) or a pharmaceutically acceptable salt thereof, comprising the following step (ii):
(ii) oxidizing a compound of formula (I-a) to produce a peptide derivative of formula (I-b) or a pharmaceutically acceptable salt thereof

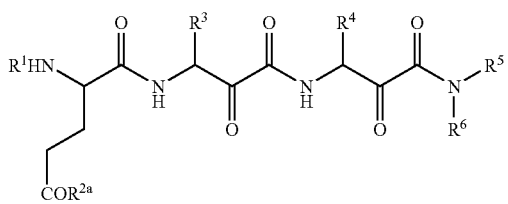
(I-b)

wherein $R^1$, $R^{2a}$, $R^3$, $R^4$, $R^5$ and $R^6$ are as defined above.

7. A process according to claim 5 for preparing a peptide derivative of formula (I) or a pharmaceutically acceptable salt thereof, comprising the following step (iii):
(iii) treating a compound of formula (I-a) with an acid to produce a peptide derivative of formula (I-c) or a pharmaceutically acceptable salt thereof

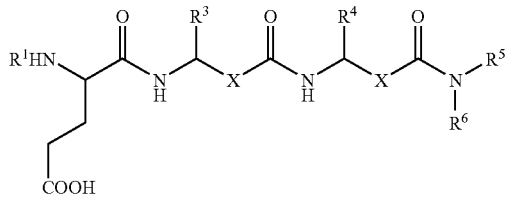
(I-c)

wherein $R^1$, $R^2$, $R^3$, $R^4$, $R^5$ and $R^6$ are as defined above, and X is —CH(OH)—.

8. A pharmaceutical preparation for periodontal disease comprising as an active ingredient at least one member selected from the group consisting of a peptide derivative of formula (I) according to claim 1 and a pharmaceutically acceptable salt thereof.

9. A composition for use in the oral cavity comprising a pharmaceutically acceptable carrier and at least one member selected from the group consisting of a peptide derivative of formula (I) according to claim 1 and a pharmaceutically acceptable salt thereof.

10. A method of preventing periodontal disease, comprising administering an effective amount of the pharmaceutical preparation for periodontal disease of claim 8 to a mammal including a human.

11. A method of preventing periodontal disease, comprising administering an effective amount of the composition for use in the oral cavity of claim 9 to a mammal including a human.

12. A method of treating periodontal disease, comprising administering an effective amount of the pharmaceutical preparation for periodontal disease of claim 8 to a mammal including a human with periodontal disease.

13. A method of treating periodontal disease, comprising administering an effective amount of the composition for use in the oral cavity of claim 9 to a mammal including a human with periodontal disease.

14. A process according to claim 6 for preparing a peptide derivative of formula (I) or a pharmaceutically acceptable salt thereof, comprising the following step (iii):
(iii) treating a compound of formula (I-b) with an acid to produce a peptide derivative of formula (I-c) or a pharmaceutically acceptable salt thereof

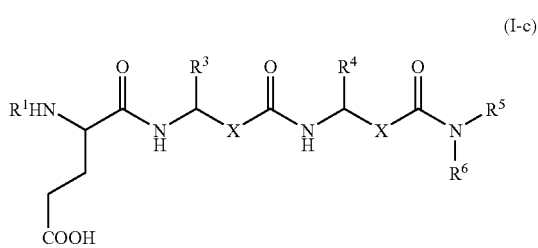
(I-c)

wherein $R^1$, $R^3$, $R^4$, $R^5$ and $R^6$ are as defined above, and X is —CO—.

* * * * *